United States Patent [19]

Wimmer et al.

[11] Patent Number: 5,302,126
[45] Date of Patent: Apr. 12, 1994

[54] DENTAL IMPLANT WITH ADJUSTABLE POST

[75] Inventors: Joachim Wimmer, Fort Lee, N.J.; Hans Baumayr, East Aurora, N.Y.

[73] Assignee: Park Dental Research Corp., New York, N.Y.

[21] Appl. No.: 854,436

[22] Filed: Mar. 19, 1992

[51] Int. Cl.⁵ .............................................. A61C 8/00
[52] U.S. Cl. .................................... 433/173; 433/174
[58] Field of Search ............... 433/173, 174, 175, 176

[56] References Cited

U.S. PATENT DOCUMENTS

| | | | |
|---|---|---|---|
| 2,112,007 | 3/1938 | Adams | 433/174 |
| 4,187,609 | 2/1980 | Edelman | 433/176 |
| 4,746,293 | 5/1988 | Lundgren et al. | 433/173 |
| 5,004,421 | 4/1991 | Lazarof | 433/173 |
| 5,015,186 | 5/1991 | Detsch | 433/173 |
| 5,049,073 | 9/1991 | Lauks | 433/173 |
| 5,092,771 | 3/1992 | Tatum, III | 433/173 |

Primary Examiner—John J. Wilson
Attorney, Agent, or Firm—Eliot S. Gerber

[57] ABSTRACT

A dental implant system includes an implant body, for example, a screw anchor having external threads or a blade, which is implanted into a pre-formed cavity in a human jaw bone. The implant body has a vertically aligned bore having an axis, a conical top face, and at least three sockets radially spaced on the top face. A post having a conical bottom face, a single protruding pin, a bore and a wall at an angle of preferably 10-30 degrees from the axis of the pin, is fastened to the implant body by a screw. The post is eccentric to the implant body and its direction is determined by which of the socket holes the dentist inserts the pin of the post.

14 Claims, 3 Drawing Sheets

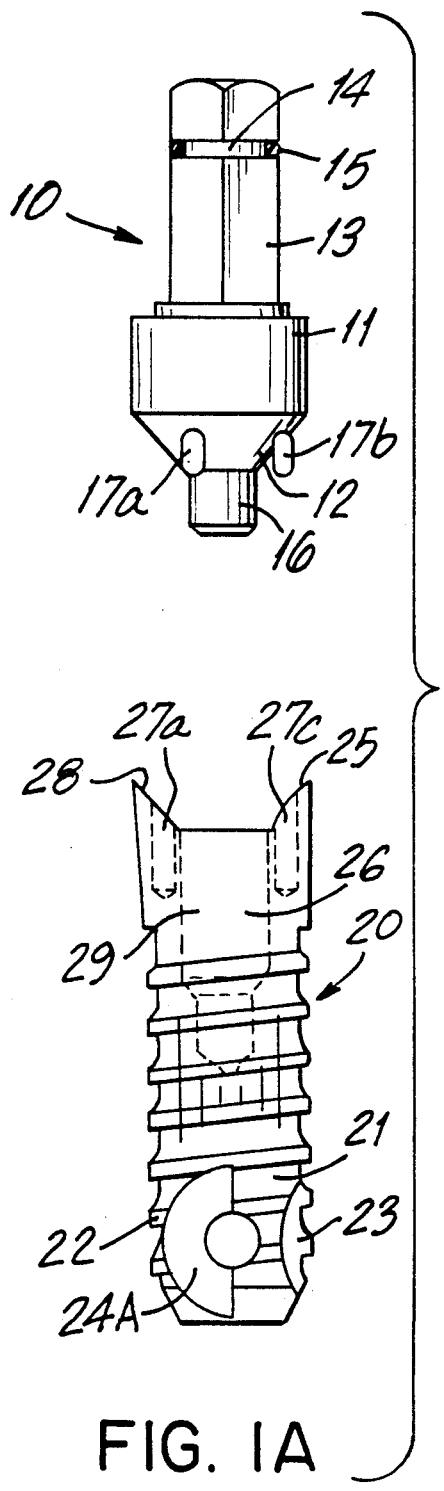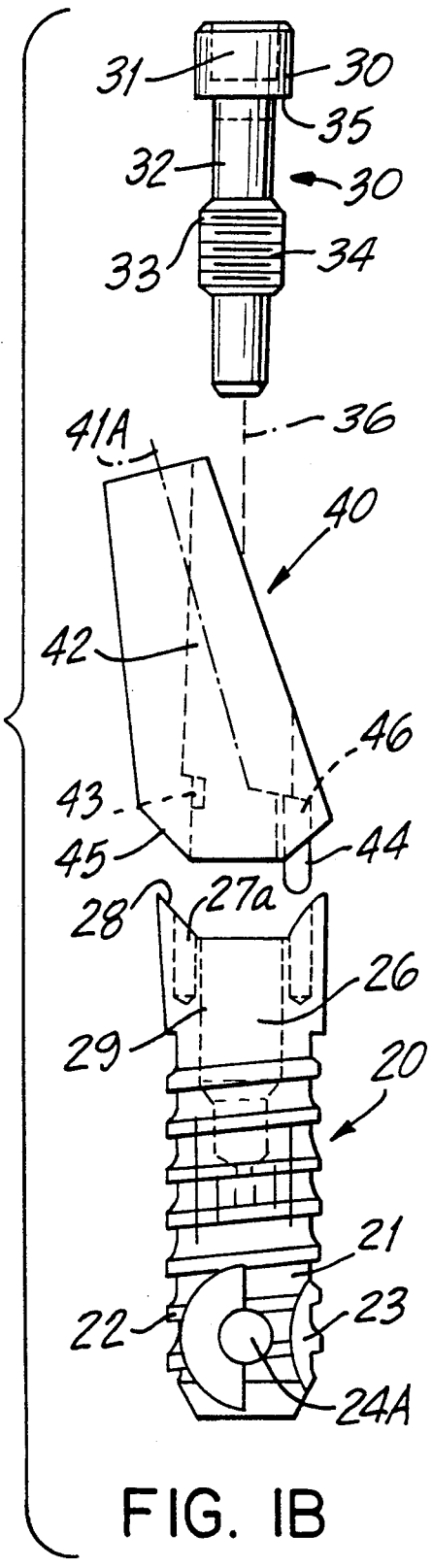
FIG. 1A
FIG. 1B

DENTAL IMPLANT WITH ADJUSTABLE POST

BACKGROUND OF THE INVENTION

1. Field of the Invention

The present invention relates to dental devices and more particularly to an endosseous dental implant system.

2. Related Art

Dental implants are generally positioned in a hole formed in the jawbone of a patient. Such implants are "endosseous" because they are retained within the bone tissue. One type of dental implant is a screw ("screw anchor") and another type is a blade. Generally such implants have a head or post which protrudes above the gum of the patient. That post is used to secure dental work such as an artificial tooth ("crown") or a bridge. Generally the implants are of biocompatible metal, such as titanium, or of a suitable ceramic material.

In U.S. Pat. No. 4,431,416 to Gerald Niznik a metal screw anchor dental implant is described which has self-tapping threads. The top of the screw anchor forms a hollow socket which holds a plastic ball and the head is attached to the ball. Although this construction provides for adjustability of the head, it is not a firm setting since the ball may be moved at any time.

There are presently on the market many types and sizes of dental implants. Often these implants are not compatible with each other, either in design or application. Sometimes, but not always, the posts (abutments) of one type of implant may be used with bridgework.

In inserting the implant in the bone, various driving techniques are employed, some of which use a hexagon driver. The mating hex socket in the implant lies either above the threaded area or is broached into the thread. When the hex is formed into the thread area, the implantologist faces the prospect of destroying the thread if too much pressure is required for insertion of the screw anchor into the bone. His second dilemma arises from a thread that is now of questionable strength to withstand the wrenching force required to obtain a solid seat for the screw so that it may withstand the mastication forces.

OBJECTIVES AND FEATURES OF THE INVENTION

The primary objective of this invention is to provide the dental implantologist with a sense of predictable control as to the angle of the post relative to the body of the implant.

It is a further objective of the present invention to provide an implant which does not compromise one feature at the expense of another, i.e., a thread with a hex broached into it.

It is a further objective to provide such an implant that addresses the complications the implantologist faces in the oral cavity trying to "feel" mating surfaces that are too small to properly see by eye.

It is a feature of the present invention to provide a dental implant system. In that system an implant body is biocompatible with human bone and adapted to be implanted in a pre-formed cavity in a human jaw bone, the implant body, for example, a screw anchor or a blade, having a bore with internal screw threads. The bore is adapted to be vertically aligned along an imaginary axis thereof after the implant body is implanted in its cavity. The implant body has a top face and at least three sockets with the sockets being radially spaced about the axis.

A post is adapted to hold a dental fixture and has a top face, a bottom face and a bore therethrough. The bore has an imaginary axis as the bore extends from the top face to the bottom face. Preferably the bottom face is conical. The post has an outer wall at a predetermined angle in the range of 5 degrees to 45 degrees, most preferably 10 degrees to 30 degrees to the post bore axis. A pin protrudes from the conical face and is inserted into a selected one of said sockets.

The fastening means is used to fasten the post to the implant body. The fastening means is preferably a screw having a screw head portion and a shaft portion. The shaft portion extends through the post bore and into the body bore. The shaft has external screw threads which are in mesh with the internal screw threads of the body bore.

BRIEF DESCRIPTION OF THE DRAWINGS

Other objectives and features of the present invention will be apparent from the following detailed description, taken in conjunction with the accompanying drawings.

In the drawings:

FIG. 1A is an exploded perspective view of the dental screw anchor implanting driver and the screw anchor;

FIG. 1B is an exploded perspective view of the dental implant screw anchor, the post and the fastening screw;

DETAILED DESCRIPTION OF THE INVENTION

Figure 9B:
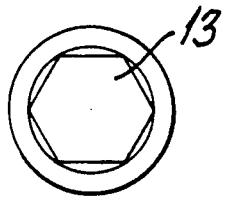
FIG. 9B is a top view of the driver of FIG. 9A.
Figure 9A:
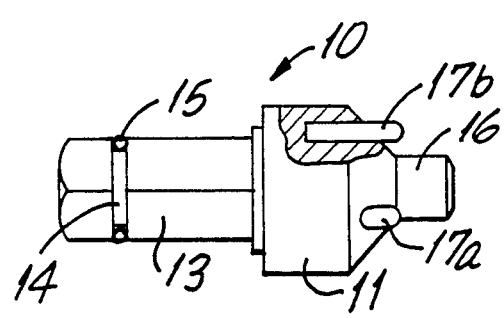
FIG. 9A shows the assembled driver in a side cross-sectional view.
Figure 9C:
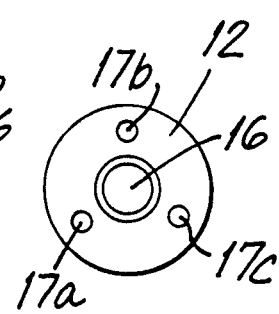
FIG. 9C is a bottom view of the driver of FIG. 9A.

As shown in FIGS. 1A and 9A-9C, a novel driver 10 is used to insert a screw anchor body into a pre-formed cylindrical hole in the patient's jaw bone. The driver 10 has a body 11 having cone-shaped face 12. As shown in FIGS. 9A-9C the body 11 is integral with a shaft 13 which is hexagonal in cross-section (see FIG. 9B). The shaft 13 has a groove 14 having a retaining C-spring 15 therein. The driver body 11 is round in cross-section and its cone-shaped face 12 has a pilot post 16, round in cross-section, for positioning the driver 10.

Three pins 17a-17c protrude from the face 16. Each of the pins 17a-17c is round in cross-section.

A tool fits on the hexagon shaft 13 so that the dentist, by operation of the tool, may apply rotative force to the shaft 13. Suitable tolls to turn shaft 13 are wrenches Nos. 009 and 010, available from Park Dental Research Corp., New York City, N.Y.

As shown in FIGS. 1A and 1B, the screw anchor 20 has a bottom end 21 having an exterior screw thread 22 which self-taps and threads into the patient's bone. The screw anchor is round in cross-section. The bottom end 21, optionally, has three exterior cuts (cutting threads) 23 and 24, providing cutting edges that form the bottom end of the screw anchor into a tap. The bottom end of the screw anchor.

The top face 25 of the screw anchor 20 (implant body) is conical and has a central bore 26 having an internal screw thread 29 and six evenly spaced small sockets 27a-27f, round in cross-section, adapted to receive the three pins 17a-17c. The implant body's top face has at least three pin receiving sockets and preferably has six such sockets and may have as many as twelve such sockets.

The screw 30 has an imaginary axis 36 and has, as integral portions thereof, a head portion 31 having therein a hexagonal socket (cavity) and a shaft portion 32 (round in cross-section) having a widened portion 33 with external screw threads 34. A shoulder 35 is formed on the bottom edge of the widened portion 33. The screw is the fastening means to fasten a post to the implant body.

The post 40 is generally eccentric (off-set) with respect to its imaginary axis 41. That axis 41 coincides with the axis 36 of the screw 30 after the screw is secured into the post 40. The post 40 has a bore 42, round in cross-section, having an inwardly protruding annular ring portion 43 to support the shoulder 35 of screw 30. The axis 41 of the bore is off-set with the imaginary axis 41A of the post. That off-set angle is in the range of 5 degrees to 45 degrees, and preferably 10 degrees to 30 degrees. Most preferably, posts having off-set angles of 15 degrees and 25 degrees are provided (FIGS. 7A, 7B, 8A and 8B). A single pin 44, round in cross-section, is fixed within a socket 46 at the bottom conical face 45 and protrudes therefrom. The bottom conical face 45 matches and fits into the conical face 25 of the screw anchor 20.

The screw 30 fastens the post 40 to the dental implant body, an example of the implant body being the screw anchor 20.

In use, the dentist will first open the gum of the patient and form a suitable cavity; for example, if a screw anchor is to be used he will drill a suitable hole in the jaw bone. The hole will be slightly undersize relative to the external screw threads of the screw anchor 20. He will then insert the screw anchor 20 using the driver 10 and turning the driver with a hand tool (not shown). The three pins 17a-17c of the driver 10 fit into the plurality of six sockets 27a-27f of the screw anchor to firmly rotate the screw anchor into the pre-drilled hole. After the screw anchor is seated, the dentist will draw away the driver. If desired, a plug of suitable material may be used to removably, and temporarily, close the bore 26 of the screw anchor, for a few weeks or months, while tissue is allowed to grow around the screw anchor 20. The plug may be removed and the post 40 fixed to the screw anchor.

The dentist selects the angle of the post 40, for example, a 15-degree post or a 25-degree post, and the angular direction of the angle. He then places the post 40 on top of the screw anchor 20 with the conical face 45 of the post fitting into the conical face 25 of the anchor 20. The dentist has selected into which of the plurality of six sockets 27a-27f he wishes the pin 44 to be inserted. That selection of the angle socket for the pin 44 determines the direction toward which the pin will be pointed. The dentist then turns the captive screw 30, with a conventional hex tool (not shown) so that its external screw threads 34 mesh with the internal screw threads 29 of the anchor 20. The screw 30 fastens the post 40 to the screw anchor 20 and the dental work, such as a partial bridge, is secured to the post.

Figure 3:
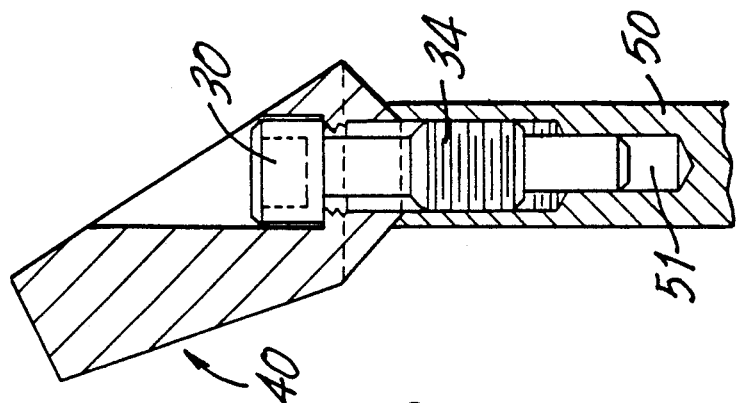
FIG. 3 is a side cross-sectional view of the post, the screw and a blade implant.
Figure 2:
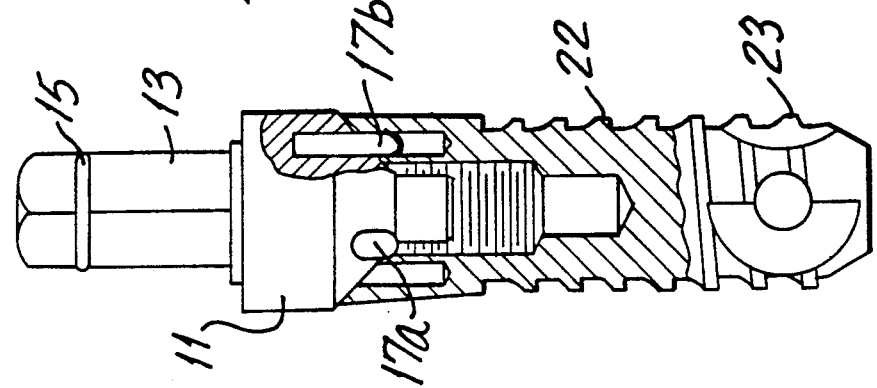
FIG. 2 is a side partial cross-sectional view of the screw anchor implant portion of FIG. 1 with the driver inserted.
Figure 7:
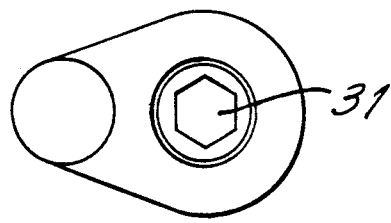
FIG. 7 is a top view of the implant of FIG. 6.
Figure 8B:
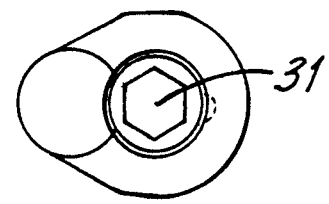
FIG. 8B is a top view of the implant of FIG. 8A.
Figure 6:
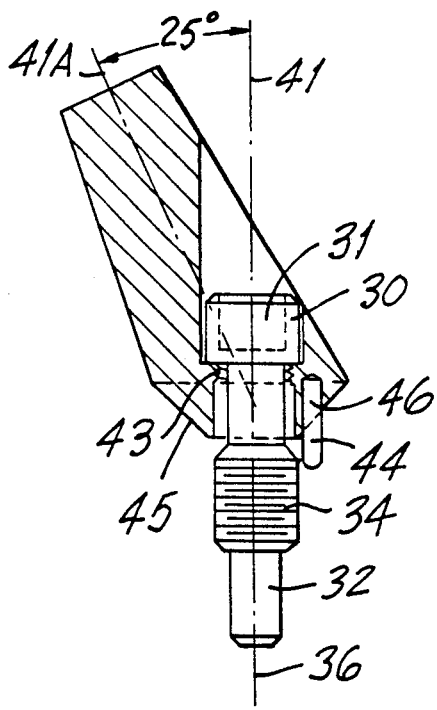
FIG. 6 is a side cross-sectional view of the screw implant with a 25-degree post attached thereto.
Figure 8A:
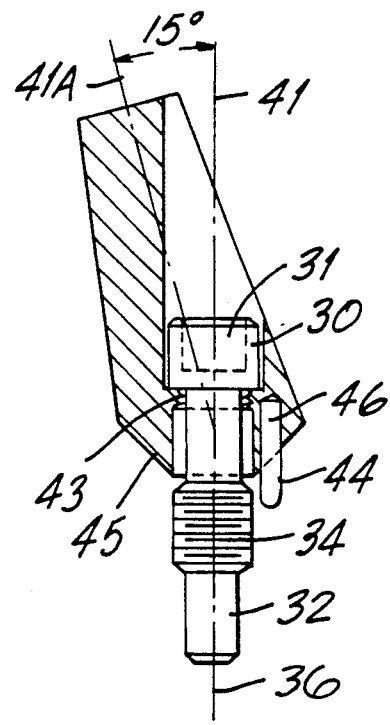
FIG. 8A is a side cross-sectional view of a screw implant with a 15-degree post.

Although the above-described embodiment is a screw anchor, the present invention is applicable to other types of dental implants. In FIG. 3 a post 40 is secured by a screw 30 to a blade implant 50 having a bore 51, at its top face. The bore 50 has internal screw threads to mesh with the external screw threads 34 of the screw 30. Blade implants are shown in U.S. Pat. No. 4,799,886 to Joachim Wimmer, incorporated by reference herein.

Figure 5:
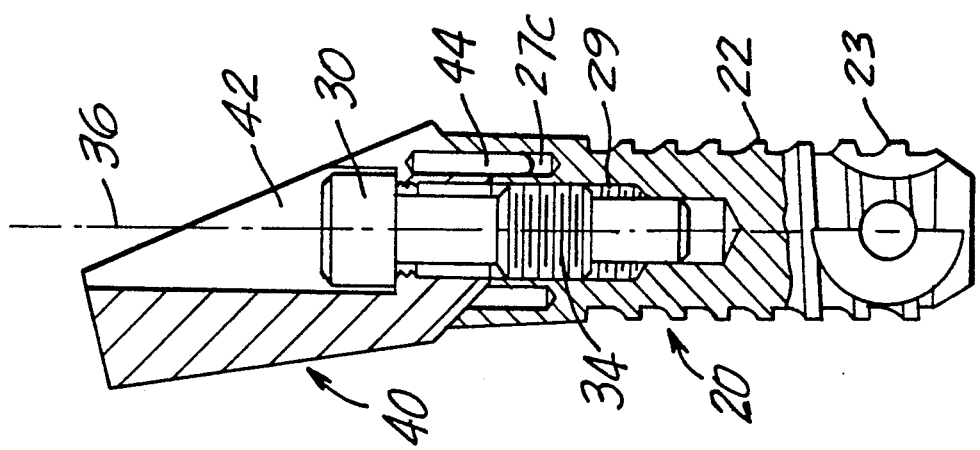
FIG. 5 is a side cross-sectional view of the screw anchor, post and fastening screw, after assembly.
Figure 4:
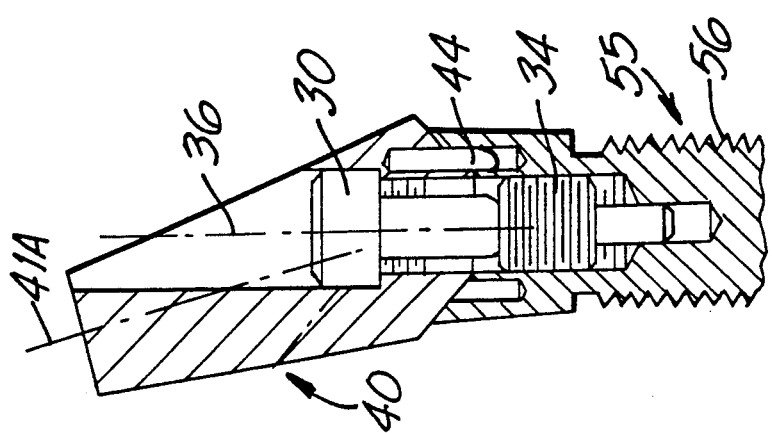
FIG. 4 is a side cross-sectional view of the post, the screw and an attachment member.

In FIG. 4 the post 40 is connected to attachment screw 55 by the screw 30. The attachment screw 55 is similar in construction to the upper portion of the screw anchor 20, in that it has a conical upper face, a central bore and smaller sockets around the central bore. However, attachment screw 55 has a machine screw thread 56 on its outer cylindrical wall, which is used to connect the attachment screw 55 to a conventional blade implant or screw anchor implant.

After assembly the post, screw and implant of the present invention are exactly aligned along their axes. A strong closing force may be applied to the screw without danger of stripping its threads, so that the post is firmly compressed, seated and stable.

What is claimed is:

1. A dental implant system comprising:
   (a) an implant body biocompatible with human bone and adapted to be implanted in a pre-formed cavity in a human jaw bone; said implant body having a bore with internal screw threads therein, said bore adapted to be vertically aligned along an imaginary axis thereof after said implant body is implanted in said cavity, said implant body having a top face having a conical portion and having said bore therethrough, and at least three sockets in said top face, said sockets being radially spaced about said axis;
   (b) a post adapted to hold a dental fixture, said post having a top face and a bottom face and a bore therethrough having an imaginary axis and extending from said top face to said bottom face; the post bottom face having a conical portion fitting against said implant body top face conical portion; said post having an outer wall at a predetermined angle in the range of 5 degrees to 45 degrees to said bore axis; and at least one pin protruding from said bottom face and being inserted into a selected one of said sockets; and
   (c) a screw having a screw head portion and a shaft portion, said shaft portion extending through said post bore and into said body bore, said shaft having external screw threads in mesh with the internal screw threads of said body bore.

2. A dental implant system as in claim 1 wherein the predetermined angle is 15 degrees.

3. A dental implant system as in claim 1 wherein the predetermined angle is 25 degrees.

4. A dental implant system as in claim 1 wherein said implant body is a screw anchor having external screw threads.

5. A dental implant system as in claim 1 wherein said implant body has at least three sockets in said top face, the sockets are round in cross-section and the sockets are evenly radially spaced about the axis of the bore of the implant body.

6. A dental implant system as in claim 1 wherein said sockets are round in cross-section.

7. A dental implant system as in claim 6 wherein said pin is a single pin which is round in cross-section.

8. A dental implant system as in claim 1 wherein said screw head portion has a hexagonal cavity therein.

9. A dental screw implant system comprising:
(a) an implant screw body biocompatible with human bone and adapted to be implanted in a pre-formed cavity in a human jaw bone; said implant screw body having a conical top face and at least two sockets in said top face, said sockets being radially spaced about an imaginary axis;
(b) a post adapted to hold a dental fixture, said post having a top face and a bottom face and a single pin having an imaginary axis; said post top face being conical and fitting against said screw body top face; said post having an outer wall at a predetermined angle in the range of 5 degrees to 45 degrees to said pin axis; said single pin protruding from said bottom face and being inserted into a selected one of said sockets; and
(c) fastening means to secure said implant screw body.

10. A dental screw implant system as in claim 9 wherein said fastening means is a screw having a screw head portion and a shaft portion, said shaft portion extending through said post and into said body, said shaft having external screw threads.

11. A dental implant system as in claim 9 wherein the predetermined angle is 15 degrees.

12. A dental implant system as in claim 9 wherein the predetermined angle is 25 degrees.

13. A dental implant screw anchor system comprising:
(a) an implant screw anchor body biocompatible with human bone having external screw threads and adapted to be screwed into a pre-formed cavity in a human jaw bone; said screw anchor having a bore with internal screw threads therein, said bore adapted to be vertically aligned along an imaginary axis thereof after said screw anchor body is implanted in said cavity, said screw anchor body having a conical top face having said bore therethrough with internal screw threads therein, at least three sockets in said top face, said sockets being radially spaced about said axis;
(b) a post adapted to hold a dental fixture, said post having a conical bottom face which fits said screw anchor body conical top face, said post having a bore therethrough with an imaginary axis extending from said top face to said bottom face; said post having an outer wall at a predetermined angle in the range of 10 degrees to 30 degrees to said post bore axis; and a single pin protruding from said bottom face and inserted into a selected one of said sockets;
(c) a screw having a screw head portion having a hexagonal cavity therein, said shaft portion extending through said post bore and into said body bore, said shaft having external screw threads in mesh with the internal screw threads of said body bore.

14. A dental implant screw anchor system comprising:
(a) an implant screw anchor body biocompatible with human bone having external screw threads and adapted to be screwed into a pre-formed cavity in a human jaw bone; said anchor body having a top face having a conical portion; a bottom end and a bore therein, said bore having cylindrical areas having a small smooth-walled diameter proximate said bottom and followed by an internal screw threaded portion of increased diameter; said top face having six sockets radially spaced about the axis;
(b) a post adapted to hold a dental fixture, said post having a bottom face with a conical bottom face portion which fits said screw anchor body conical top face portion, said bottom face having a bore therethrough with an imaginary axis extending from said top face to said bottom face about which is positioned a smooth-walled cylinder, the bore of the post also having a short internal scrwethreaded portion; said post having an outer wall at a predetermined angle in the range of 10 degrees to 30 degrees to said post bore axis; and a single pin protruding from said bottom face and inserted into a selected one of said sockets;
(c) a screw having a shaft portion and a screw head portion having a turning means therein, said shaft portion extending through said post bore and into said body bore, said shaft portion having external screw threads in mesh with the internal screw threaded portion of said body bore.

* * * * *